(12) United States Patent
Trivedi et al.

(10) Patent No.: US 8,541,420 B2
(45) Date of Patent: Sep. 24, 2013

(54) KETOLIDE COMPOUNDS HAVING ANTIMICROBIAL ACTIVITY

(75) Inventors: Bharat Kalidas Trivedi, Farmington Hills, MI (US); Mahesh Vithalbhai Patel, Aurangabad (IN)

(73) Assignee: Wockhardt Ltd., Bandra-Kurla Complex, Bandra East, Mumbai (IN)

( * ) Notice: Subject to any disclaimer, the term of this patent is extended or adjusted under 35 U.S.C. 154(b) by 49 days.

(21) Appl. No.: 13/321,892

(22) PCT Filed: May 26, 2010

(86) PCT No.: PCT/IB2010/052325
§ 371 (c)(1),
(2), (4) Date: Feb. 4, 2012

(87) PCT Pub. No.: WO2010/136971
PCT Pub. Date: Dec. 2, 2010

(65) Prior Publication Data
US 2012/0142710 A1 Jun. 7, 2012

(30) Foreign Application Priority Data
May 27, 2009 (IN) .......................... 1307/MUM/2009

(51) Int. Cl.
*C07D 239/24* (2006.01)
*C07D 403/14* (2006.01)
*C07D 417/14* (2006.01)
*A61K 31/443* (2006.01)

(52) U.S. Cl.
USPC .......... 514/256; 514/338; 544/333; 546/268.7

(58) Field of Classification Search
USPC ............... 514/256, 338; 544/333; 546/268.7
See application file for complete search history.

(56) References Cited

FOREIGN PATENT DOCUMENTS

| WO | WO2004096823 A2 | 11/2004 |
| WO | WO2008023248 A2 | 2/2008 |

*Primary Examiner* — Samantha Shterengarts
(74) *Attorney, Agent, or Firm* — Bio Intellectual Property Services LLC (Bio IPS); O. M. Sam Zaghmout

(57) ABSTRACT

The invention relates to ketolide compound of Formula-I and the pharmaceutically acceptable salts thereof having antimicrobial activity. The invention also provides pharmaceutical compositions containing the compounds of invention and methods of treating or preventing microbial infections with the compound of invention.

8 Claims, No Drawings

KETOLIDE COMPOUNDS HAVING ANTIMICROBIAL ACTIVITY

FIELD OF THE INVENTION

The invention relates to ketolide compound of Formula-I and the pharmaceutically acceptable salts thereof having antimicrobial activity. The invention also provides pharmaceutical compositions containing the compounds of invention and methods of treating or preventing microbial infections with the compound of invention.

BACKGROUND OF THE INVENTION

Ketolides, a well-known family of antimicrobial agents, are semisynthetic 14-membered ring macrolide derivatives, characterized by the presence of a keto function at position 3 instead of L-cladinose moiety present in the macrolactone ring. Telithromycin and Cethromycin are examples of ketolides.

Telithromycin is described in U.S. Pat. No. 5,635,485 and *Bioorg. Med. Chem. Lett.* 1999, 9(21), 3075-3080. Another ketolide Cethromycin (ABT 773) and other are disclosed in PCT application No. WO 98/09978, and *J. Med. Chem.* 2000, 43, 1045.

The U.S. Pat. No. 6,900,183 describes 11,12-ylactone ketolides having C-21 of the lactone substituted with cyano or amino derivatives. The patent applications such as U.S. 2004/0077557 and PCT publications WO 02/16380, WO 03/42228, WO 03/072588 and WO 04/16634 disclose 11,12-γ lactone ketolides. Our co-pending PCT application No. WO 08/023248 discloses several Macrolides and Ketolides.

The ketolide compounds of the invention bearing a thiadiazole heteroaryl in the side chain are useful antimicrobial agent. The compounds of invention have shown unexpectedly superior potency against the Gram-positive bacteria including the macrolide and ketolide resistant strains. Remarkebly, compounds of the invention are characterized by superior oral effectiveness in the treatment of resistant microbial infections.

SUMMARY OF THE INVENTION

The invention relates to ketolide compounds of Formula-I,

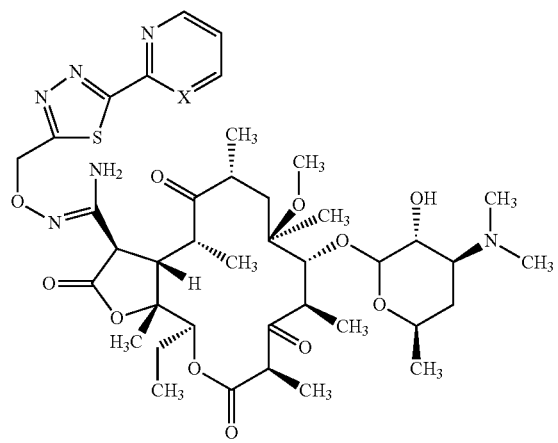

Formula I wherein
X is CH or N; and
the pharmaceutically acceptable salts thereof.

The invention also provides pharmaceutical composition containing a compound of Formula-I and a pharmaceutically acceptable carrier, diluent or excipients thereof.

The invention further provides a method of treating or preventing a microbial infection, employing compound of Formula-I.

The details of one or more embodiments of the invention are set forth in the description below. Other features, objects and advantages of the invention will be apparent from the description and claims.

DETAIL DESCRIPTION OF THE INVENTION

In one general aspect there is provided ketolide compounds of Formula-I

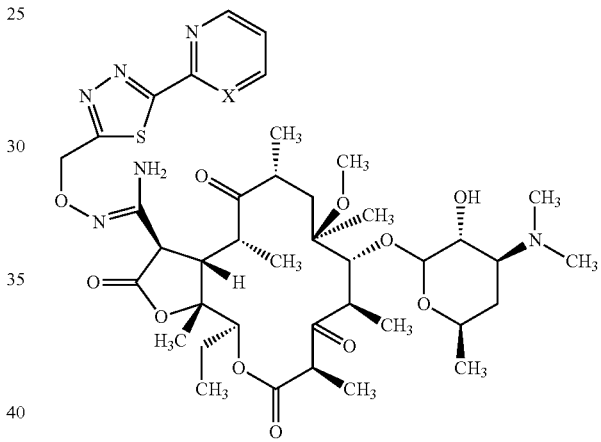

Formula-I wherein
X is CH or N; and
the pharmaceutically acceptable salts thereof.
Description of the Terms:

The following definitions are used, unless otherwise described.

The term "pharmaceutically acceptable salt" as used herein refers to one or more salts of the free base of the invention which possess the desired pharmacological activity of the free base and which are neither biologically nor otherwise undesirable. The salts are suitable for use in contact with the tissues of human and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 66: 1-19 (1977), incorporated herein by reference. The salts can be prepared in situ during the final isolation and purification of the compounds of the invention, or separately by reacting the free base function with a suitable acid. These salts may be obtained from inorganic or organic acids. Examples of inorganic acids are hydrochloric acid, nitric acid, perchloric acid, hydrobromic acid, sulphuric acid or phosphoric acid. Examples of organic acids are acetic acid, propionic acid, oxalic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulphonic acid, p-toluene sulphonic acid, salicyclic acid and the like. Also included are the salts with various amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine or the optically active isomers thereof or the racemic mixtures thereof or dipeptides, tripeptides and polypeptides derived from the monoaminoacid units thereof.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malonate, 2-naphthalenesulfonate, nicotinate, oleate, palmitate, pamoate, pectinate, persulfate, 3-phenylpropionate, phosphate, picrate, pivalate, propionate, stearate, sulfate, tartrate, thiocyanate, p-toluenesulfonate, undecanoate, valerate salts, and the like.

Salt of an acid moiety in the compound can also be prepared by reacting with a suitable base. These suitable salts are furthermore those of the inorganic or organic bases. Inorganic bases such as KOH, NaOH, Ca (OH)$_2$, Al(OH)$_3$. The organic base salts from basic amines such as ethylamine, triethylamine, diethanolamine, ethylenediamine, guanidine or heterocyclic amines such as piperidine, hydroxyethylpyrrolidine, hydroxyethylpiperidine, morpholine, piperazine, N-methyl piperazine and the like or basic amino acids such as optically pure and racemic isomers of arginine, lysine, histidine, tryptophan and the like.

Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

The term "Therapeutically effective amount" means that amount of active compound(s) or pharmaceutical agent(s) that elicit the biological or medicinal response in a tissue system, animal or human sought by a researcher, veterinarian, medical doctor or other clinician, which response includes alleviation of the symptoms of the disease or disorder being treated. The specific amount of active compound(s) or pharmaceutical agent(s) needed to elicit the biological or medicinal response will depend on a number of factors, including but not limited to the disease or disorder being treated, the active compound(s) or pharmaceutical agent(s) being administered, the method of administration, and the condition of the patient.

The term "treatment" unless otherwise indicated, includes the treatment or prevention of a microbial infection as provided in the method of the present invention.

The term "microbial infection(s)" includes but not limited bacterial infections may be caused by Gram-positive, Gram-negative bacteria, aerobic, anaerobic bacteria, atypical bacteria or protozoa that may be treated or prevented by administering antibiotics such as the compounds of the invention. Such bacterial infections and protozoa infections and disorders related to such infections include the following: pneumonia, otitis media, sinusitis, bronchitis, tonsillitis, and mastoiditis related to infection by *Streptococcus pneumoniae, Haemophilus influenzae, Moraxella catarrhalis, Staphylococcus aureus*, or *Peptostreptococcus* spp.; pharynigitis, rheumatic fever, and glomerulonephritis related to infection by *Streptococcus* pyogenes, Groups C and G streptococci, *Clostridium diptheriae*, or *Actinobacillus haemolyticum;* respiratory tract infections related to infection by *Mycoplasma pneumoniae, Legionella pneumophila, Streptococcus pneumoniae, Haemophilus influenzae*, or *Chlamydia pneumoniae;* uncomplicated skin and soft tissue infections, abscesses and osteomyelitis, and puerperal fever related to infection by *Staphylococcus aureus*, coagulase-negative staphylococci (i.e., *S. epidermidis, S. hemolyticus*, etc.), *Streptococcus pyogenes, Streptococcus agalactiae*, Streptococcal groups C-F (minute-colony streptococci), viridans streptococci, *Corynebacterium minutissimum, Clostridium* spp., or *Bartonella henselae;* uncomplicated acute urinary tract infections related to infection by *Staphylococcus saprophyticus* or *Enterococcus* spp.; urethritis and cervicitis; and sexually transmitted diseases related to infection by *Chlamydia trachomatis, Haemophilus ducreyi, Treponema pallidum, Ureaplasma urealyticum*, or *Neiserria gonorrheae;* toxin diseases related to infection by *S. aureus* (food poisoning and Toxic shock syndrome), or Groups A, B, and C streptococci; ulcers related to infection by *Helicobacter pylori;* systemic febrile syndromes related to infection by *Borrelia recurrentis;* Lyme disease related to infection by *Borrelia burgdorferi;* conjunctivitis, keratitis, and dacrocystitis related to infection by *Chlamydia trachomatis, Neisseria gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare;* gastroenteritis related to infection by *Campylobacter jejuni;* intestinal protozoa related to infection by *Cryptosporidium* spp.; odontogenic infection related to infection by viridans streptococci; persistent cough related to infection by *Bordetella pertussis;* gas gangrene related to infection by *Clostridium perfringens* or *Bacteroides* spp.; and atherosclerosis related to infection by *Helicobacter pylori* or *Chlamydia pneumoniae*. Bacterial infections and protozoa infections and disorders related to such infections that may be treated or prevented in animals include the following: bovine respiratory diseases related to infection by *P. haem., P. multocida, Mycoplasma bovis*, or *Bordetella* spp. or *Haemophilus* spp.; or protozoa (i.e., coccidia, cryptosporidia, etc.); dairy cow mastitis related to infection by *Staph. aureus, Strep. uberis, Strep. agalactiae, Strep. dysgalactiae*, or *Enterococcus* spp.; swine respiratory disease related to infection by *A. pleuro., P. multocida*, or *Mycoplasma* spp.;, *Lawsonia intracellularis, Salmonella*, or *Serpulina hyodyisinteriae;* cow footrot related to infection by *Fusobacterium* spp.; cow hairy warts related to infection by *Fusobacterium necrophorum* or *Bacteroides nodosus;* cow pink-eye related to infection by *Moraxella bovis;* cow premature abortion related to infection by protozoa (i.e. neosporium); skin and soft tissue infections in dogs and cats related to infection by *Staph. epidermidis*, *Staph. intermedius*, coagulase neg. *Staph.* or *P. multocida*; and dental or mouth infections in dogs and cats related to infection by *Alcaligenes* spp., *Bacteroides* spp., *Clostridium* spp., *Eubacterium, Peptostreptococcus, Porphyromonas*, or *Prevotella*.

The compounds of invention includes:
(11S,21R)-3-Decladinosyl-11,12-dideoxy-6-O-methyl-3-oxo-12,11-{oxycarbonyl-[E-amino-(2-(pyridin-2-yl)-1,3,4-thiadiazol-5-yl-methyl)oxy-imino-methylene]}-erythromycin A; and
(11S,21R)-3-Decladinosyl-11,12-dideoxy-6-O-methyl-3-oxo-12,11-{oxycarbonyl-[E-amino-(2-(pyrimidin-2-yl)-1,3,4-thiadiazol-5-yl-methyl)oxy-imino-methylene]}-erythromycin A.

In an embodiment, the invention provides process for the preparation of ketolide compounds of Formula-I and pharmaceutically acceptable salts thereof.

The following schemes describe the preparation of the compounds of Formula-I of the invention. All of the starting materials are prepared by procedures that would be well known to one of ordinary skill in organic chemistry.

The process of preparation of ketolide compounds of Formula-I and pharmaceutically acceptable salts thereof includes following two steps.

Step I) Procedure for Side Chain Synthesis lamine or pyridine in a suitable solvent such as dichloromethane or dichloroethane or chloroform or tetrahydrofuran (THF) or mixture thereof, at a temperature ranging from −5° C. to 50° C., after which the solvent is optionally changed to suitable solvent such as tetrahydrofuran or 1,4-dioxane or toluene or xylene mixture thereof, and the reaction mixture is treated with Lawesson's reagent at a temperature ranging from 30° to 140° C., to provide corresponding heteroaryl-1,3,4-thiadiazolyl-carboxylic acid alkyl ester compound 3. The compound 3 is reacted with reducing agent such as sodium borohydride or lithium borohydride in a suitable solvent such as methanol or ethanol or tetrahydrofuran (THF) or water or mixture thereof, at a temperature ranging from −5° C. to 50° C., preferably 0° C. to 35° C. to provide corresponding heteroaryl-1,3,4-thiadiazolyl-methanol compound 4.

The compound 4 is reacted with alkyl or aryl sulfonyl chloride such as methanesulfonyl chloride or p-tolylsulfonylchloride in the presence of organic base such as triethylamine, diisopropylethylamine or pyridine in a suitable solvent such as dichloromethane or dichloroethane or chloroform or tetrahydrofuran (THF) or mixture thereof, at a temperature ranging from −10° C. to 40° C., to provide corresponding alkyl or aryl sulfonate ester of heteroaryl-1,3,4-thiadiazolyl-

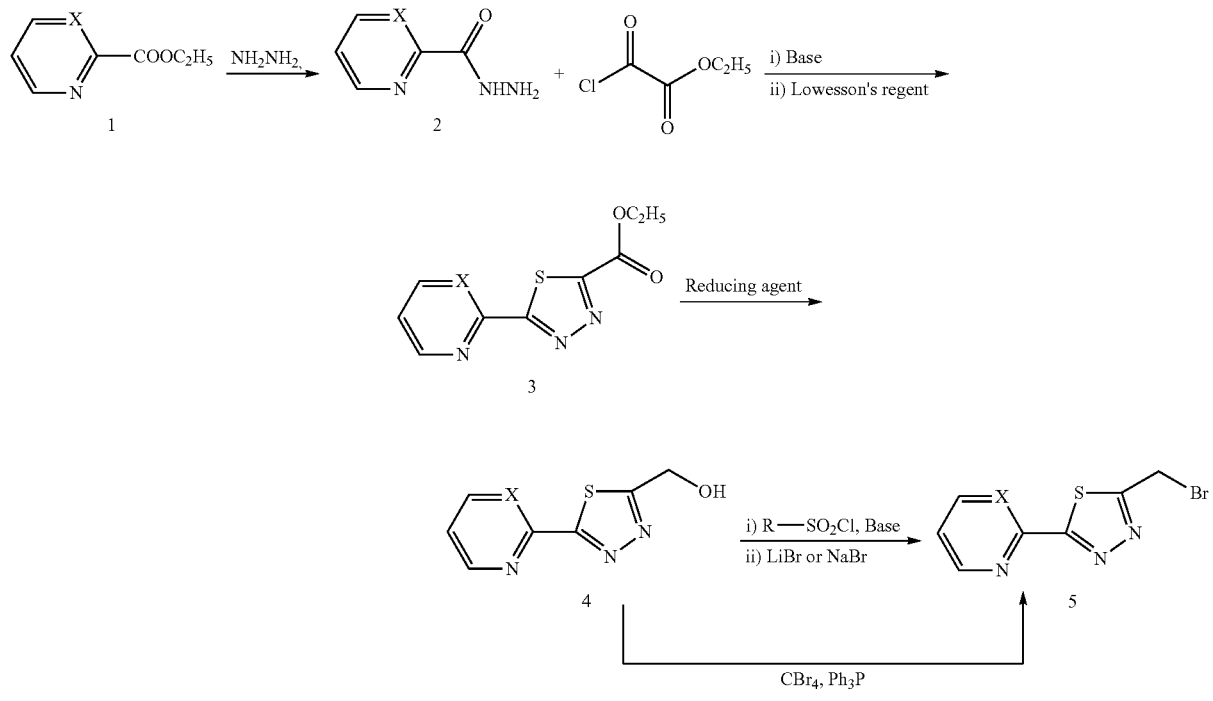

X = CH or N

As detailed in Scheme-1, alkyl ester of 2-pyridine or 2-pyrimidine carboxylic acid 1 is reacted with hydrazine in a suitable solvent such as methanol or ethanol or water or mixture thereof, at a temperature ranging from 20° to 100° C. to provide corresponding compound 2. The compound (2) is treated with mono ethyl ester of oxalyl chloride in the presence of organic base such as triethylamine, diisopropylethylamine or pyridine in a suitable solvent such as dichloromethane or dichloroethane or chloroform or tetrahydrofuran (THF) or mixture thereof, at a temperature ranging from −5° C. to 50° C., to provide corresponding heteroaryl-1,3,4-thiadiazolyl-methanol, which is further reacted with lithium bromide or sodium bromide, in a suitable solvent such as acetone or 2-butanone, at temperature ranging from 40° C. to 80° C., to provide corresponding heteroaryl-1,3,4-thiadiazolyl-methyl bromide compound 5. Optionally, heteroaryl-1,3,4-thiadiazolyl-methyl bromide compound 5 is prepared by reacting heteroaryl-1,3,4-thiadiazolyl-methanol compound 4 with carbon tetrabromide along with phosphine reagent such as triphenylphosphine tritolylphosphine, in a suitable solvent such as dichloromethane or dichloroethane or chloroform at a temperature ranging from −10° C. to 40° C.

Step II) Procedure for Ketolide Synthesis (pyrimidinyl/pyridyl)-1,3,4-thiadiazolyl-methyl bromide in the presence of suitable organic base such as potassium hydride or potassium tertbutoxide or potassiumhexamethyldisilazane base or inorganic base such as potassium hydroxide without or with phase transfer catalyst such as 18-crown-6

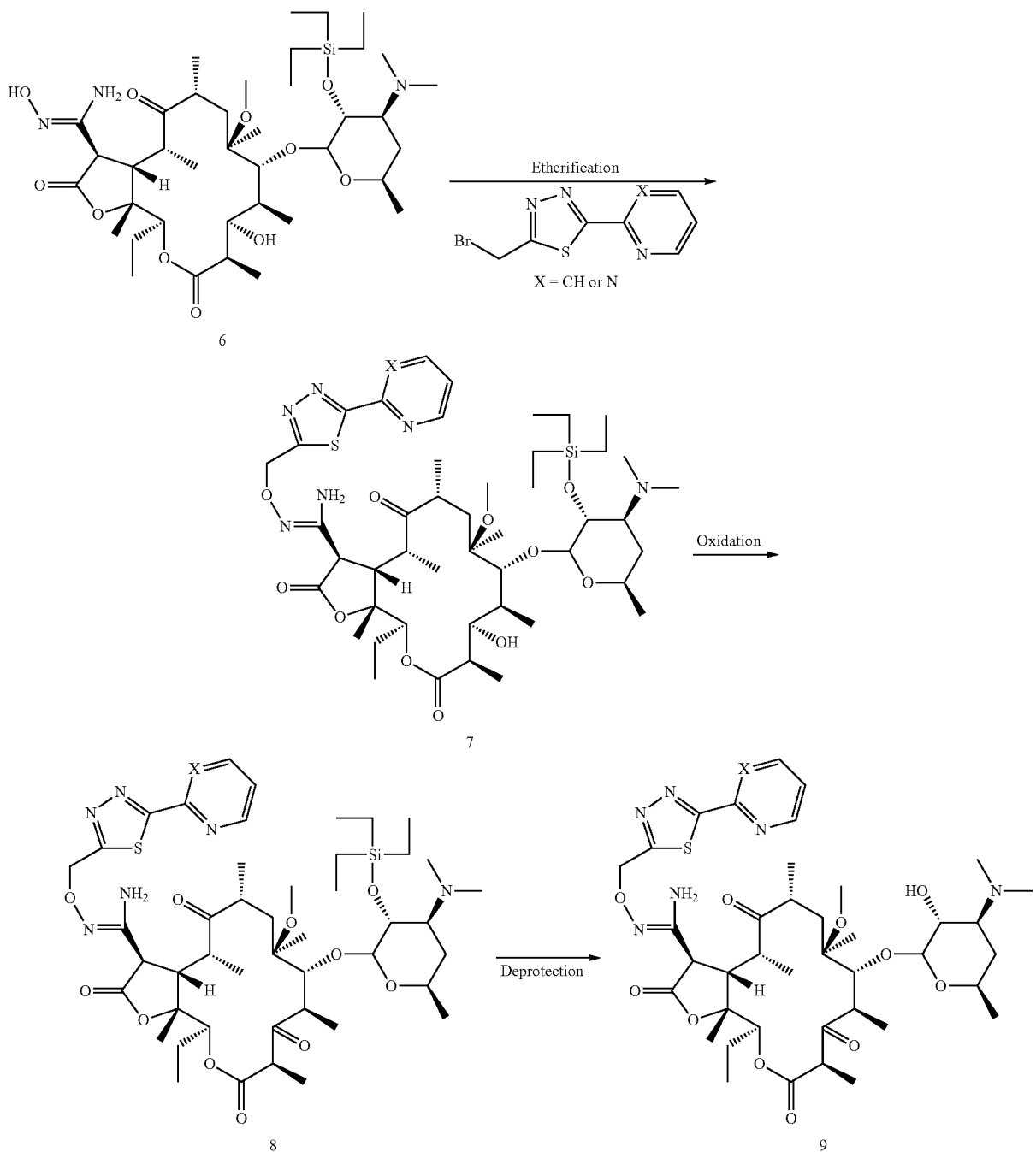

Scheme-2

As detailed in scheme-2, (11S, 21R)-2'-O-triethylsilyl-3-decladinosyl-11,12-dideoxy-6-O-methyl-12,11-1-{oxycarbonyl-[(E-amino(hydroxyimino)methyl]}-erythromycin A (6) prepared as per the procedure described in a PCT application No. WO 08/023248 A2, is reacted with appropriate ether or tetrabutylammoniumbromide in a suitable solvent such as benzene or toluene or xylene, at a temperature ranging from −10° C. to 50° C., to provide etherified compound 7.

Compound 7 is oxidized by treating under standard condition using either Corey-Kim oxidizing species or with Dess- Martin periodinane reagent, in a suitable solvent such as dichloromethane or dichloroethane or chloroform, at a temperature ranging from −50° C. to 10° C., to provide a 2'-2'-O-triethylsilyl protected ketolide compound 8. Compound 8 is then reacted with silyl deprotecting agent such as pyridine-hydrogenfluoride, tetrabutylammonium fluoride, hydrochloric acid, in a suitable solvent such as acetonitrile or tetrahydrofuran or dioxane, at a temperature ranging from 0° C. to 40° C., to provide the ketolide compound 9 of the invention.

In another aspect, the invention also provides pharmaceutical composition comprising ketolide compounds of Formula-I and pharmaceutically acceptable salts thereof and a pharmaceutically acceptable carrier, diluent or excipient therefore. As used herein, such a "pharmaceutically acceptable" component is one that is suitable for use with humans and/or animals without undue adverse side effects (such as toxicity, irritation, and allergic response) commensurate with a reasonable benefit/risk ratio.

In a specific embodiment of the invention, the pharmaceutical compositions contain a therapeutically effective amount of the ketolide compounds of the invention and pharmaceutically acceptable salts thereof described in this specification as hereinbefore described in association with a pharmaceutically acceptable carrier, diluent or excipients, and optionally other therapeutic ingredients.

For the purpose of this invention, the pharmaceutical compositions contain the compounds of the invention, in a form to be administered in admixture with a pharmaceutical carrier selected with regard to the intended route of administration and standard pharmaceutical practice. Suitable carriers which can be used are, for example, diluents or excipients such as fillers, extenders, binders, emollients, wetting agents, disintegrants, surface active agents and lubricants which are usually employed to prepare such drugs depending on the type of dosage form.

Any suitable route of administration may be employed for providing the patient with an effective dosage of the compounds of the invention. For example, oral, rectal, vaginal, parenteral (subcutaneous, intramuscular, intravenous), nasal, transdermal, topical and like forms of administration may be employed. Suitable dosage forms include tablets, pills, powders, troches, dispersions, solutions, suspensions, emulsions, capsules, injectable preparations, patches, ointments, creams, lotions, shampoos, and the like.

In yet another aspect of invention provides a method for treating or preventing microbial infections in a patient, comprising administering to said patient a therapeutically effective amount of a ketolide compounds of Formula-I and pharmaceutically acceptable salts thereof.

The compounds of invention have shown unexpectedly superior potency against the Gram-positive bacteria including the specific macrolide and ketolide resistant strains.

Remarkebly, compounds of the invention are characterized by superior oral effectiveness in the treatment of resistant microbial infections.

The prophylactic or therapeutic dose of the ketolide compounds of Formula-I and pharmaceutically acceptable salts thereof, in the acute or chronic management of disease will vary with the severity of condition to be treated, and the route of administration. In addition, the dose, and perhaps the dose frequency, will also vary according to the age, body weight and response of the individual patient. In general, the total daily dose range, for the compounds of the invention, for the conditions described herein, is from about 10 mg to about 5000 mg. It may be necessary to use dosages outside these ranges in some cases as will be apparent to those skilled in the art.

Further, it is noted that the clinician or treating physician will know how and when to interrupt, adjust, or terminate therapy in conjunction with individual patient's response.

The term patient as used herein is taken to mean birds, fishes and mammals, for example, humans, cats, dogs, horses, sheep, bovine cows, pigs, lambs, rats, mice and guinea pigs.

The invention is further illustrated by the following examples which are provided merely to be exemplary of the invention and do not limit the scope of the invention. Certain modifications and equivalents will be apparent to those skilled in the art and are intended to be included within the scope of the invention.

EXAMPLES

The following examples describe in detail the chemical synthesis of some of the representative compounds of the present invention. The procedures are illustrations, and the invention should not be construed as being limited by chemical reactions and conditions they express. No attempt has been made to optimize the yields obtained in these reactions, and it would be obvious to one skilled in the art that variations in reaction times, temperatures, solvents, and/or reagents could increase the yields.

Example 1

(11S, 21R)-3-Decladinosyl-11,12-dideoxy-6-O-methyl-3-oxo-12,11-{oxycarbonyl-[E-amino-(2-(pyridin-2-yl)-1,3,4-thiadiazol-5-yl-methyl)oxy-imino-methylene]}-erythromycin A Step-1: Etherification To the stirred solution of potassium hydride (4.50 g, 30% suspension in mineral oil), 18-crown-6-ether (1.0 g) and (11S,21R)-2'-O-triethylsilyl-3-decladinosyl-11,12-dideoxy-6-O-methyl-12,11-{oxycarbonyl-[(E-amino(hydroxyimino) methyl]}-erythromycin A (25 g) in toluene (500 ml) was added followed by 2-(5-bromomethyl-1,3,4-thiadiazol-2-yl)-pyridine (9.78 gm) at 30° C. temperature. The reaction mixture was stirred for 30 minutes. The reaction mixture was quenched by adding aqueous saturated ammonium chloride solution (100 ml). The mixture was extracted with ethyl acetate (250 ml×2). Layers were separated. Combined organic layer was evaporated under vacuum to provide a step-1 product in 16.0 gm (52%) as off white solid.

MS=(m/z)=961.3 (M+1)

Step-2: Oxidation

To the stirred solution of N-chlorosuccinimide (16.62 gm) in dichloromethane (200 ml) was added dimethyl sulfide (15.31 ml) at −15° C. The reaction mixture was stirred at −15° C. for 30 min. The step-1 product (16 gm) dissolved in dichloromethane (200 ml) was added to the reaction mixture at −40° C. The resulting reaction mixture was stirred at −40° C. temperature for 3 hr. Triethyl amine (60 ml) was added and stirred for overnight at 30° C. The reaction mixture was poured in aqueous saturated sodium bicarbonate solution (200 ml) and layers were separated. The combined organic layer was dried over $Na_2SO_4$ and evaporated under vacuum to provide crude mass which was purified by using silica gel column chromatography (15% acetone: hexane) to provide 2'-O-triethylsilyl protected ketolide as a step-2 compound in 13.55 gm (84%) quantity as a white foam after silica gel column chromatography.

Mass: m/z: 959.4 (M+1)

Step-3: Deprotection

The mixture of step-2 product (13.5 gm) and 70% HF-pyridine solution (0.800 ml) in acetonitrile (150 ml) was stirred at 30° C. for 2 h under $N_2$ atmosphere. Saturated aqueous sodium bicarbonate solution was added (50 ml) to the reaction mixture and it was stirred for 15 minutes. The mixture was evaporated to one fourth of its volume under vacuum. The resulting suspension was stirred with water (50 ml) to provide precipitation and the solid was filtered under suction. The wet cake was washed water followed by diethyl ether. It was vacuum dried at 60° C. to provide the ketolide compound of the invention in 9.5 gm (80%) quantity as off white solid.

Mp=208.5° C. (by DSC)

Mass: m/z: 845.3 (M+1)

HPLC purity: 94.41% (single isomer) at retention time 11.92 minutes (HPLC system: Column: ACE 5 C18, 250×4.6 mm, mobile phase: a mixture of 0.05 M ammonium acetate buffer (pH adjusted to 5.5 by acetic acid) and acetonitrile in 60:40 ratio, flow rate: 1.0 ml/min, wavelength 215 nm, run time 40 minutes, sample prepared in 1 mg/ml in 1:1 acetonitrile water mixture.

The following preparations illustrate the preparation of starting materials used in the synthesis of example-1.

Preparation 1:
2-(5-Bromomethyl-1,3,4-thiadiazol-2-yl)-pyridine

Step-1: Pyridin-2-carboxylic acid hydrazide

A mixture of ethyl pyridin-2-carboxylate (90 gm) and hydrazine hydrate (60 gm) in ethanol (400 ml) was stirred at 80° C. over a period of 4 h. Solvent was evaporated and to provide a crude mass. The mass was stirred with diethyl ether and the suspension was filtered and the wet cake washed with small quantity of ethanol (50 ml) to provide title compound in 76 gm quantity (93%) as a white solid.

Mass: m/z: 138.0 (M+1)

Step-2: 2-(5-Ethoxycarbonyl-1,3,4-thiadiazol-2-yl)-pyridine

To a mixture of pyridin-2-carboxylic acid hydrazide (76 gm), triethylamine (155 ml) in dichloromethane (600 ml) was added mono ethyl ester of oxalyl chloride (80 gm) over a period of 0.5 h at 0° C. The reaction mixture was stirred for 2 h. The reaction was monitored by TLC. The reaction was quenched by addition of water (100 ml), layers were separated and organic layer was washed with aqueous sodiumbicarbonate solution (100 ml). Organic layer was evaporated in vacuum to provide crude mass in 110 gm quantity. To a crude mass in tetrahydrofurane (500 ml) was added Lowesson's reagent (208 gm) and the mixture was stirred at 60° C. over a period of 4 h. Solvent was evaporated and the crude mass was triturated with dicholomethane ether mixture. The suspension was filtered and the wet cake washed with small quantity of methanol (100 ml) to provide title compound in 45 gm quantity (35% after 2 steps) as off white solid.

Mass: m/z: 236.0 (M+1)

1H NMR: (400 Mhz, $CDCl_3$): 1.36 (t, 3H), 4.32 (q, 2H), 7.52 (m, 1H), 7.91 (m, 1H), 8.28 (d, 1H), 8.60 (d, 1H).

Step-3: 2-(5-Hydroxymethyl-1,3,4-thiadiazol-2-yl)-pyridine

To a mixture of 2-(5-ethoxycarbonyl-1,3,4-thiadiazol-2-yl)-pyridine (8 gm), in ethanol (80 ml) was added sodium borohydride (2.51 gm) in lots at 30° C. It was stirred at 30° C. over a period of 2 h. The reaction was monitored by TLC. The solvent was evaporated under vacuum to provide a crude mass. To the crude mass water (100 ml) was added and it was extracted with dichloromethane (200 ml×2). Combined organic layers was washed with water and concentrated under vacuum to provide title compound in 6.1gm quantity (92%). It as used as without purification for the next reaction.

Mass: m/z: 194.0 (M+1)

1H NMR: (400 Mhz, DMSO $d_6$): 4.88 (d, 2H), 6.24 (br s, 1H, exchangable), 7.55 (m, 1H), 8.02 (m, 1H), 8.24 (d, 1H), 8.69 (d, 1H).

Step-4: 2-(5-Methanesulfonyloxymethyl-1,3,4-thiadiazol-2-yl)-pyridine

To a mixture of 2-(5-hydroxymethyl-1,3,4-thiadiazol-2-yl)-pyridine (6 gm), and triethylamine (13.1 ml) in dichloromethane (150 ml) was added methanesulfonylchloride (5.31 gm) at 0° C. The reaction mixture was stirred at 0° C. over a period of 1 h. The reaction was quenched by addition of water and layers were separated. Aqueous layer was extracted with dichloromethane. Combined organic layer was washed with aqueous sodium bicarbonate solution followed by water and evaporated under vacuum to provide title compound in 7.5 gm quantity (88%) as oil.

Mass: m/z: 272.0 (M−1)

Step-5: 2-(5-Bromomethyl-1,3,4-thiadiazol-2-yl)-pyridine

A mixture of 2-(5-methansulfonuloxymethyl-1,3,4-thiadiazol-2-yl)-pyridine (7.5 gm), lithium bromide (3.84 gm) in acetone (75 ml) was stirred at reflux over a period of 1 h. The reaction was monitored by TLC. The reaction mixture was evaporated under vacuum to provide a crude mass. Crude mass was stirred with ice cold water to provide a suspension. The solid was filtered under suction to afford the title compound in 6.5 gm quantity (92%) as a light brownish solid.

Mass: m/z: 255.0 (M+1)

1H NMR: (400 Mhz, DMSO $d_6$): 5.16 (s, 2H), 7.59 (m, 1H), 8.03 (m, 1H), 8.24 (d, 1H), 8.70 (d, 1H).

Example-2

(11S,21R)-3-Decladinosyl-11,12-dideoxy-6-O-methyl-3-oxo-12,11-{oxycarbonyl-[E-amino-(2-(pyrimidin-2-yl)-1,3,4-thiadiazol-5-yl-methyl)oxy-iminomethylene]}-erythromycin A Step-1: Etherification By using procedures described in step-1 of Example-1 and using (11S,21R)-2'-O-triethylsilyl-3-decladinosyl-11,12-dideoxy-6-O-methyl-12,11-{oxycarbonyl-[(E-amino(hydroxyimino)methyl]}-erythromycin A (2.5 g) and 2-(5-bromomethyl-1,3,4-thiadiazol-2-yl)-pyrimidine (0.9 gm) in the place of 2-(3-bromomethyl-isoxazol-5-yl)-pyrimidine, step-1 compound was obtained in 2.4 gm (78.4%) quantity as a solid.

Mass: m/z: 962.4 (M+1)

Step-2: Oxidation

By using procedures described in step-2 of Example-1 and by using step-1 compound of Example-3 (12 gm) the ketolide compound as a step-2 product was obtained in 6.4 gm (53.5%) quantity as a white solid after silica gel column chromatography.

Mass: m/z: 960.3 (M+1)

Step-3: Deprotection

By using procedures described in step-3 of Example-1 and by using step-2 compound of Example-2 (6.4 gm) the ketolide compound of the invention was obtained in 4.5 gm (79.8%) quantity as off white solid.

Mp=158-160° C.

Mass: m/z: 846.3 (M+1)

HPLC purity: 93.94% (single isomer) at retention time 12.83 minutes (HPLC system: Column: ACE C18, 25 cm, mobile phase: a mixture of 0.05 M ammonium acetate buffer (pH adjusted to 7.0 by acetic acid) and acetonitrile in 65:35 ratio, flow rate: 1.0 ml/min, wavelength 260 nm, run time 50 minutes, sample prepared in 1 mg/ml in 1:1 acetonitrile water mixture.

The following preparations illustrate the preparation of starting materials used in the synthesis of example-2.

Preparation 2:
2-(5-Bromomethyl-1,3,4-thiadiazol-2-yl)-pyrimidine

Step-1: Pyrimidin-2-carboxylic acid hydrazide

A mixture of ethyl pyrimidin-2-carboxylate (100 gm) and hydrazine hydrate (50 ml in ethanol (500 ml) was stirred at 30° C. over a period of 14 h. The suspension was filtered at suction and the wet cake washed with small quantity of ethanol (25 ml) followed by diethyl ether (50 ml) to provide title compound in 80 gm quantity (88%) as a white solid.

Mass: m/z: 139.0 (M+1)

1H NMR: (400 Mhz, DMSO $d_6$): 4.60 (br s, 2H, exchangeable), 7.64 (t, 1H), 8.91 (d, 2H), 10.00 (br s, 1H, exchangeable)

Step-2: 2-(5-Ethoxycarbonyl-1,3,4-thiadiazol-2-yl)-pyrimidine

To a mixture of pyrimidin-2-carboxylic acid hydrazide (50 gm), triethylamine (75 ml) in tetrahydrofuran (1.5 Ltr) was added mono ethyl ester of oxalyl chloride (52.20 gm) over a period of 0.5 h at 10° C. to 15° C. The reaction mixture was allowed to warm and stirred for 0.5 h at 30° C. To the reaction mixture was added Lowesson's reagent (219 gm) at 40° and the mixture was refluxed over a period of 4 h. The reaction mixture was cooled to 30° C. and filtered at suction. The filtrate was concentrated to provide a residue which was stirred with ethyl acetate (500 ml). The suspension was filtered at suction and the wet cake washed with small quantity of ethyl acetate (25 ml) to provide title compound in 30 gm quantity (35% after 2 steps) as white solid.

Mass: m/z: 237.0 (M+1)

1H NMR: (400 Mhz, CDCl$_3$): 1.49 (t, 3H), 4.58 (m, 2H), 7.46 (t, 1H), 8.94 (d, 2H).

Step-3: 2-(5-Hydoxymethyl-1,3,4-thiadiazol-2-yl)-pyrimidine

To a mixture of 2-(5-ethoxycarbonyl-1,3,4-thiadiazol-2-yl)-pyrimidine (30 gm), in 1% aqueous ethanol (500 ml) was added sodium borohydride (5.0 gm) in lots at 25° to 30° C. It was stirred at 30° C. over a period of 3 h. The solvent was evaporated under vacuum to provide a crude mass. To the crude mass water (ml) was purified by using silica gel column chromatography to provide title compound in 15 gm quantity (60%) as pale yellow solid.

Mass: m/z: 195.0 (M+1)

Step-4: 2-(5-Methanesulfonyloxymethyl-1,3,4-thiadiazol-2-yl)-pyrimidine

To a mixture of 2-(5-hydroxymethyl-1,3,4-thiadiazol-2-yl)-pyrimidine (15 gm) and triethylamine (22 ml) in dichloromethane (250 ml) was added methanesulfonylchloride (7.2 ml) at 0° C. The reaction mixture was stirred at 0° C. over a period of 1 h. The reaction was quenched by addition of water and layers were separated. Aqueous layer was extracted with dichloromethane (200 ml×2). Combined organic layer was washed with aqueous sodium bicarbonate solution followed by water and evaporated under vacuum to provide title compound in 20.1 gm quantity (quantitative) as oil.

Mass: m/z: 273.0 (M+1)

Step-5: 2-(5-Bromomethyl-1,3,4-thiadiazol-2-yl)-pyrimidine

A mixture of 2-(5-methansulfonuloxymethyl-1,3,4-thiadiazol-2-yl)-pyrimidine (15 gm), lithium bromide (6.4 gm) in acetone (100 ml) was stirred at reflux over a period of 4 h. The reaction mixture was evaporated under vacuum to provide a crude mass. Crude mass was stirred with ice cold water to provide a suspension. The solid was filtered under suction to afford the title compound in 9.2 gm quantity (66%) as a light brownish solid.

Mass: m/z: 259.0 (M+2)

1H NMR: (400 Mhz, CDCl$_3$): 4.87 (s, 2H), 7.43 (t, 1H), 8.91 (d, 2H).

As noted above, the compounds of the invention are useful as antimicrobials. The compounds of the invention are active against the macrolide and ketolide resistant strains of Gram positive bacteria. The following experiments were conducted to determine potency of the compounds of the invention against Gram positivebacteria. The results of the experiments are tabulated below.

Biological Protocols: Evaluation of Ketolides

The antibacterial activities of ketolide compounds of invention were evaluated by determining the minimal inhibitory concentration (MIC) according to standard CLSI agar dilution method. The media used for preculture and main culture were Tryptic Soya broth (Difco) and Mueller Hinton medium (Difco), respectively. The Mueller Hinton agar was supplemented with 5% sheep blood for streptococci and pneumococci, and with haemoglobin as well as NAD (nicotinamide adenine dinucleotide) for *Haemophilus influenzae*, respectively. Overnight cultures were diluted with buffered saline (pH 7.2) to the final cell density of $5 \times 10^6$-$10^7$ CFU/ml, and each bacterial suspension was applied with a replicator (Denley's multipoint inoculator, UK) onto a series of Mueller-Hinton agar plates containing antibacterial agents at various concentrations. Final inoculum was approximately $10^4$ CFU/spot. The plates were incubated for 18 hrs at 37° C. The MIC was defined as the lowest concentration of an antibacterial agent that inhibits the development of visible microbial growth on agar.

Results

Antibacterial Activity: Macrolide Sensitive and Resistant *S. pyogenes* (MIC Tests)

| | S. pyogenes | | | |
|---|---|---|---|---|
| Example No | Ery Susc. (801) | ermTR (810/806) | HLermB (3530) | mefA (806/763) |
| 1 | 0.015 | 0.015 | 0.5 | 0.06 |
| 2 | 0.007 | 0.015 | 0.25 | 0.06 |
| Telithromycin | 0.03 | 0.03 | 16.0 | 0.06 |

Note:
HL is High level resistance

Antibacterial Activity: Macrolide Sensitive and Resistant *S. pneumoniae* (MIC Tests)

| Example No | *S. pneumoniae* | | | |
|---|---|---|---|---|
| | Ery Susc. (49619) | ermB (786) | HL-ermB (3773) | mefA (772) |
| 1 | 0.007 | 0.06 | 1.0 | 0.06 |
| 2 | 0.007 | 0.06 | 1.0 | 0.25 |
| Telithromycin | 0.007 | 0.5 | 4.0 | 1.0 |

Note:
HL is High level resistance

The invention claimed is:

1. A ketolide compound of Formula-I,

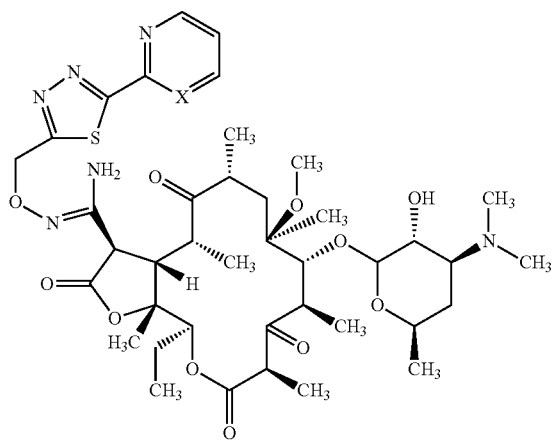

Formula-I wherein X is CH or N; or a pharmaceutically acceptable salts thereof.

2. The ketolide compound as claimed in claim 1, selected from:
 (11S,21R)-3-Decladinosyl-11, 12-dideoxy-6-O-methyl-3-oxo-12, 11-{oxycarbonyl-[E-amino-(2-(pyridin-2-yl)-1,3,4-thiadiazol-5-yl-methyl)oxy-imino-methyl-ene]}-erythromycin A; and
 (11S,21R)-3-Decladinosyl-11,12-dideoxy-6-O-methyl-3-oxo-12, 11-{oxycarbonyl-[E-amino-(2-(pyrimidin-2-yl)-1,3,4-thiadiazol-5-yl-methyl)oxy-imino-methyl-ene]}-erythromycin A.

3. A pharmaceutical composition comprising a therapeutically effective amount of a compound of the Formula-I or a pharmaceutically acceptable salt thereof as claimed in claim 1, in association with a pharmaceutically acceptable carrier, excipient or diluent.

4. A pharmaceutical composition comprising a therapeutically effective amount of a compound as claimed in claim 2, in association with a pharmaceutically acceptable carrier, excipient or diluent.

5. A method of treating microbial infections, comprising administering to a patient suffering from a microbial infection, a therapeutically effective amount of a compound of the Formula-I as claimed in claim 1.

6. A method of treating microbial infections, comprising administering to a patient suffering from a microbial infection, a therapeutically effective amount of a compound as claimed in claim 2.

7. A method of treating microbial infections, comprising administering to a patient suffering from a microbial infection, a composition as claimed in claim 3.

8. A method of treating microbial infections, comprising administering to a patient suffering from a microbial infection, a composition as claimed in claim 4.

* * * * *